United States Patent [19]

Ando

[11] Patent Number: 4,686,565

[45] Date of Patent: Aug. 11, 1987

[54] METHOD AND APPARATUS FOR VISUALLY EXAMINING AN ARRAY OF OBJECTS DISPOSED IN A NARROW GAP

[75] Inventor: Moritoshi Ando, Atsugi, Japan

[73] Assignee: Fujitsu Limited, Kawasaki, Japan

[21] Appl. No.: 735,744

[22] Filed: May 20, 1985

[30] Foreign Application Priority Data

May 22, 1984 [JP] Japan ................................ 59-104249

[51] Int. Cl.⁴ .............................................. H04N 7/18
[52] U.S. Cl. .................... 358/101; 358/106; 350/506; 350/445; 356/392; 356/394; 356/376; 250/572
[58] Field of Search ............... 356/237, 388, 394, 376, 356/379, 392; 350/506, 507, 445, 447, 287; 358/101, 107, 106; 382/8; 250/572

[56] References Cited

U.S. PATENT DOCUMENTS 4,028,728  6/1977  Sharp .................................. 358/106
4,473,842  9/1984  Suzuki et al. ....................... 358/107

Primary Examiner—Howard W. Britton
Assistant Examiner—John K. Peng
Attorney, Agent, or Firm—Staas & Halsey

[57] ABSTRACT

A method of and apparatus for visual inspection of the condition of soldered connections between connector pads of a wiring pattern provided on a circuit board and tips of conductor pins of an IC package mounted thereby on the circuit board. The back, or bottom surface of the circuit board is illuminated by a flood of light to produce diffused, or scattered, light in the gap between the circuit board and the IC package, which diffused light is emitted from the edge of the gap. The emitted light is deflected by a small prism disposed adjacent the edge of the gap into a focusing means, such as a stereoscopic microscope having a long focal distance and an optical axis oriented substantially perpendicularly to the surface of the circuit board. Images of the soldered connections are observeable through the eyepiece of the microscope, or are detected by a photoelectric transducer such as a video camera for display on a video screen.

21 Claims, 14 Drawing Figures

METHOD AND APPARATUS FOR VISUALLY EXAMINING AN ARRAY OF OBJECTS DISPOSED IN A NARROW GAP

BACKGROUND OF THE INVENTION

1. Field of the Invention

The present invention relates to a method and apparatus for visually examining an array of objects disposed in a narrow gap and, more specifically, to such a method and apparatus wherein the array of objects to be visually examined are arranged to extend transversely of a small gap defined by parallel plates, one of which is light transmitting.

2. State of the Prior Art

As is well known, integrated circuit ("IC") packages conventionally are mounted on a substrate or circuit board, typically a printed circuit board ("PCB"), electrical connection being made between output leads of the IC package and corresponding connector pads of the latter formed as part of a wiring pattern on the PCB. As the trend continues toward large scale integration ("LSI") of such IC packages, the number of electrical connections which must be effected is increasing dramatically.

Currently, the most popular and most extensively employed packaging technology for conventional IC's is that known as DIP (dual inline package) and variations or equivalents thereof, wherein plural leads are formed so as to extend in generally parallel relationship from the parallel, longer side surfaces of the generally rectangluar IC package, transversely to the bottom surface of the DIP. Typically, in present usage, the largest number of leads formed on such an IC package or DIP, is 64; with current technology, it is difficult to contemplate that the number could be increased to any substantial extent, such as to 100 or more such leads.

Accordingly, there has been an effort to overcome the limitation in the maximum number of leads which are available for the conventional IC's, directed primarily to using the back surface of the package. An exemplary packaging technology directed to this configuration is disclosed in the Japanese patent application of the Provisional Publication Tokkaisho No. 59-151443, published August 29, 1984 (corresponding to U.S. Pat. application Ser. No. 579,127, filed February 10, 1984). In accordance with the technology disclosed in the referenced Japanese and corresponding U.S. patent applications, as many as 200 or more leads, or conductor pins, are secured to corresponding conductor pads formed on the back surface of the package, so as to extend in generally parallel relationship with one another downwardly from the back surface and in a substantially perpendicular relationship thereto. For convenience of terminology, the conductor pins are characterized as "vertical" in reference to a nominal "horizontal" orientation of the backside surface of the package. The IC package then is placed on a circuit board such that the free ends, or tips, of the conductor pins contact corresponding conductor pads associated with a wiring pattern formed on the circuit board, the pins then being connected to the pads by soldering. This type of packaging technology advantageously permits increasing the packing density of IC's on a circuit board.

Circuit boards having IC's mounted thereon, sometimes referred to as "cards," generally are subjected to a visual inspection of the condition of the soldered connections between each of the pins and the corresponding pads, prior to being subjected to functional electrical tests. The visual inspection is important to eliminate latent defects, or faults of the cards which may occur due to poor, or defective, soldered connections, which can result in faulty operation which otherwise might not become apparent until operation of system incorporating the cards in field testing.

The conventional visual inspection procedure for examining the condition of the soldered connections, however, is not applicable to cards comprising IC's fabricated and mounted on circuit boards in accordance with the packaging technology disclosed in the referenced patent applications. The reason is that the soldered joints or connections are hidden in the small gap between the package and the PCB on which it is mounted, and thus cannot be observed directly, either from the top side (i.e., through the package itself) or from the backside of the circuit board (i.e., the surface of the PCB opposite that on which the package is mounted). By contrast, in the case of cards comprising conventional IC's of the DIP type, for example, the condition of the soldered connections can be examined readily by observing the corresponding through holes on the back surface of the card. Accordingly, it is crucial to the practical use of IC's, based on the packaging technology disclosed in the referenced applications, that a new method of visual examination be provided to examine the condition of the soldered connections of the connecting pins and the respective, corresponding pads.

SUMMARY OF THE INVENTION

A primary object of the present invention, therefore, is to provide a method and apparatus to enable the visual examination and inspection of the condition of soldered connections between the tips of conductor pins, extending from the back surface of an IC package in an array of more than two rows, and the corresponding conductor pads formed in a wiring pattern of a circuit board on which the IC package is mounted.

A further object of the present invention is to provide a method and apparatus permitting visual examination of a plurality of objects arranged to extend transversely of a small gap defined by substantially flat, inner surfaces of first and second generally parallel, spaced plates, wherein one of the plates is light transmissible and has parallel inner and outer surfaces.

In accordance with the invention, these and other objects and advantages are achieved through the provision of an apparatus providing for and a method of visual examination of plural objects such as conductor pins extending transversely through a small gap defined between first and second, spaced and generally parallel plates, which may comprise, respectively, a light transmitting PCB and the backside surface of an IC, and particularly for examining the condition between the tips of the conductor pins and the corresponding conductor pads formed on the PCB. For this purpose, the apparatus comprises a means for illuminating the outer surface of the first, light transmitting plate so as to produce scattered light in the gap therebetween, which is then emitted from the edge of the gap defined between the second parallel plate and the first. The apparatus further comprises means for deflecting the light emitted from the edge of the gap in a direction substantially perpendicular to the inner surface of the first plate, and means for focusing the light thus emitted and deflected, to form an image of each object. The corresponding method of the present invention thus comprises the steps of illuminating the outer surface of the first, light transmitting plate so as to produce scattered light within the gap, deflecting the light which is emitted from an edge of the gap in a direction substantially perpendicular to the inner surface of the first plate, and focusing the emitted light to form an image of each object within the gap.

BRIEF DESCRIPTION OF THE DRAWINGS

The above and other objects and advantages of the present invention will be more apparent from the following detailed description of the preferred embodiments with reference to the accompanying drawings, wherein.

DETAILED DESCRIPTION OF THE PREFERRED EMBODIMENT

Figure 1A:
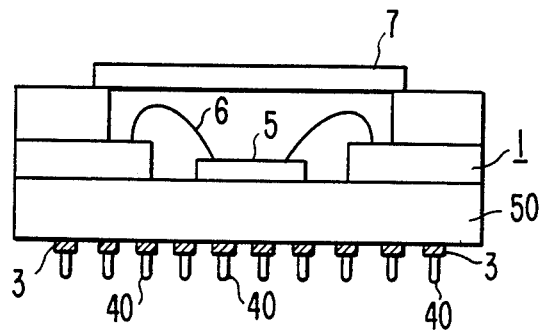
FIG. 1A is a cross-sectional view of an exemplary structure of an IC package, corresponding to that disclosed in the above-referenced U.S. patent application.
Figure 1B:
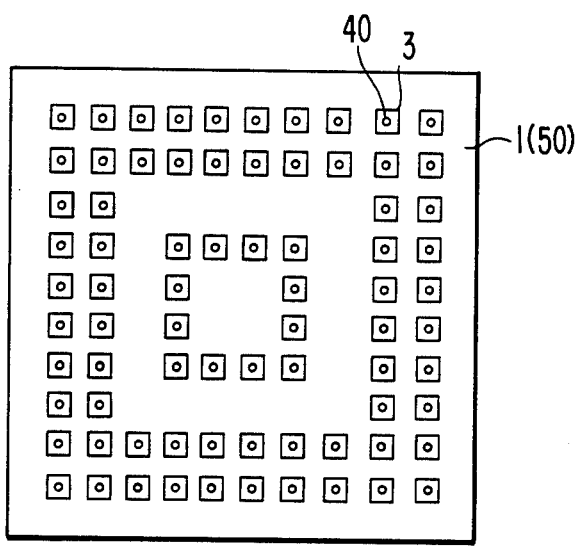
FIG. 1B is a plan view illustrating the back, or bottom, surface of the IC package shown in FIG. 1A.

To better understand the present invention, and thus prior to setting forth a detailed description of a preferred embodiment thereof, further explanations are first provided of the packaging technology disclosed in the above-referenced U.S. patent application, in relation to FIGS. 1A and 1B herein. Further, the parameters which must be taken into account, for enabling the visual examination of the soldered connections in accordance with the apparatus and method of the present invention, will be explained with reference to the schematic illustration of an IC package mounted on a circuit board as shown in FIG. 2 hereof.

FIG. 1A is a simplified elevational view, illustrating the structure of an IC package as disclosed in the above-referenced U.S. patent application. The IC package 1 comprises a semiconductor chip 5 formed on a substrate 50 and a cap 7. A plurality of conductor pads 3, shown in cross-section for improved illustration in the figure, may be formed from a metallized layer provided on the back, or bottom surface of the substrate 50. As better seen in the plan view of FIG. 1B, which illustrates the back, or bottom surface of the substrate 50, the conductor pads 3 are disposed generally in a matrix arrangement, and individual ones thereof are connected to corresponding terminals (not shown) formed on the periphery of the chip 5 through lead wires 6. The conductor pins 40 are connected to corresponding conductor pads 3 of the matrix arrangement formed on the substrate 50 by a brazing technique, and arranged thereon so as to extend transversely to the back surface of the substrate 50 and thus substantially in a veritical orientation relative to the substrate 50 when disposed in a horizontal position as in FIG. 1A. The conductor pins 40 thus comprise the outer leads of the IC package 1, and may be 100 or more in number.

Figure 2:
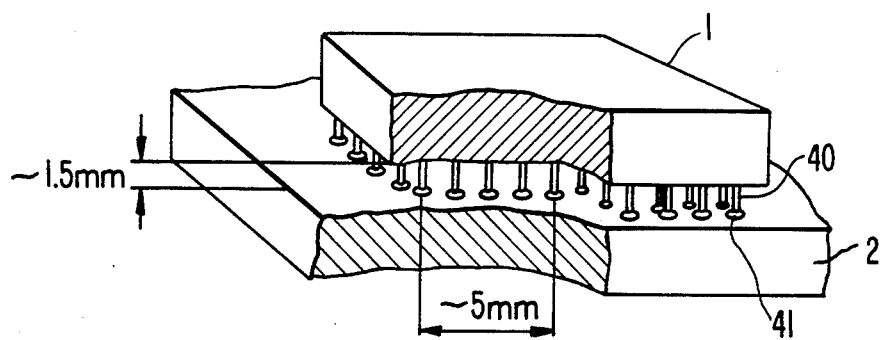
FIG. 2 is a partially cut-away perspective view illustrating the IC package shown in FIG. 1A, as mounted on a circuit board.

FIG. 2 is a partially cutaway, perspective and simplified view of the IC package 1 of FIG. 1A, mounted on a circuit board 2. As therein illustrated, the IC package 1 is mounted on the circuit board 2 such that the tip of each conductor pin 40 contacts a corresponding conductor pad and is electrically and mechanically connected thereto by a layer of solder, the solder joint being generally designated at 41. Typically, a solder layer is formed on the pad in advance of the assembly operation and the elements are juxtaposed with the tips of the conductor leads 40 abutting the solder layer of the corresponding pads. Heat then is applied to the thus assembled and abutting conductor leads 40 and corresponding conductor pads, such as by blowing hot air thereover; the solder at each conductor pad thus melts and spreads upwardly, wetting the surface of the conductor pin 40 and forming an electrical and mechanical bond between the conductor pin 40 and the pad of the associated wiring pattern (not shown) on the circuit board 2. With regard to typical dimensions and spacial relationships, the conductor pins 40 each may be of 1.5 mm in length and successive ones thereof may be arranged at a pitch of about 1.25 mm. The gap between the opposed surfaces of the IC package 1 and the circuit board 2 may be about 1.5 mm. Five rows of the conductor pins 40 may be arranged in a zone width of about 5 mm along each side of the IC package 1.

Figure 3A:
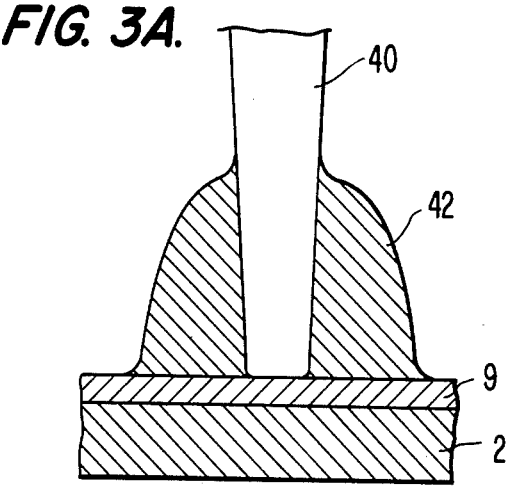
FIGS. 3A, 3B and 3C are schematic illustrations, on a microscopically, greatly enlarged scale, of cross-sectional views of soldered connections, in differing conditions, between connector pins of the IC package, such as that in FIG. 1A, and corresponding conductor pads of a circuit board on which such an IC package is mounted, as shown in FIG. 2.
Figure 3B:
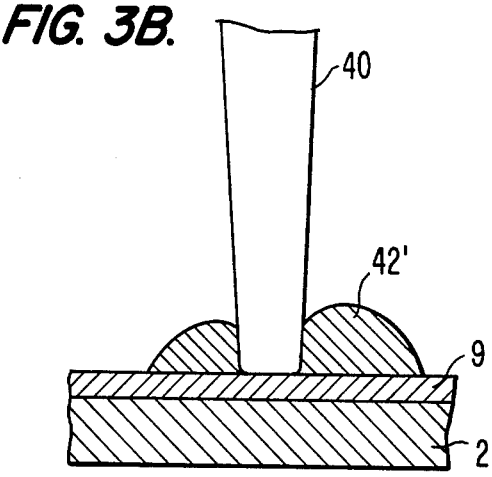
Figure 3C:
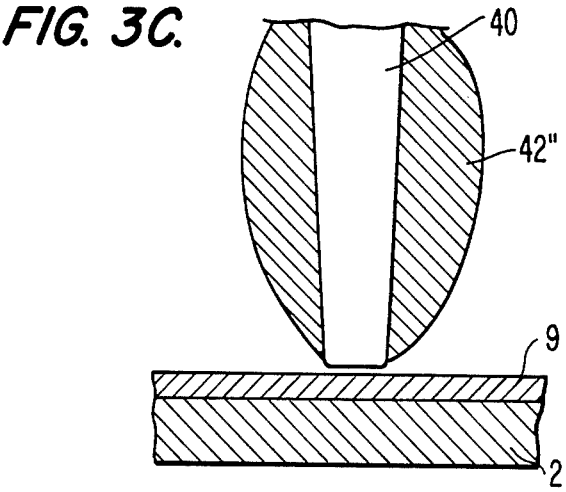

FIGS. 3A, 3B and 3C are views, partly in cross-section and on a greatly enlarged, e.g., microscopically enlarged, scale, illustrating varying conditions of the soldered connections which may be formed between a conductor pin 40 and a connector pad 9 of a wiring pattern formed on a printed circuit board 2. Particularly, FIG. 3A illustrates the desired condition, or configuration, of a soldered joint or connection 42 beween the conductor pin 40 and the conductor pad 9, wherein the solder has properly wetted the conductor pin 40 and thus assumes a bell-shaped profile. Conversely, as shown in FIG. 3B for the case in which the solder does not wet the surface of the conductor pin 40 adequately, there results a solder joint or connection 42', having a double-humped profile, in which the surface of the solder joint 42' forms a large contact angle with the surface of the conductor pin 40. A further condition is illustrated in FIG. 3C, in which the solder joint or connection 42'' satisfactorily wets the surface of the conductor pin 40, but does not wet the surface of the conductor pad 9 properly. This produces a spindle-shaped profile, in which the solder effectively has transfered completely to the conductor pin 40 and thus is withdrawn from the conductor pad 9; in the extreme case shown in FIG. 3C, both the mechanical bonding and, necessarily, the electrical bonding between the conductor pin 40 and the pad 9 altogether fail.

As before mentioned, and with regard to the poor soldered condition illustrated in FIG. 3B, even though the potentially defective electrical connection is not revealed as a problem during factory tests, failure in field operations sometimes results. Hence, visual examination of the condition of the soldered connection is highly significant, for eliminating latent faults resultant from poor solder joints.

Accordingly, the present invention is directed to providing apparatus for, and a method of, inspecting the condition of soldered connections of each conductor pin 40 and corresponding connector pad 9 by observing the profile of the soldered connection, relative to those profiles as are illustrated in FIGS. 3A, 3B and 3C. As is apparent from FIG. 2, that visual examination must be performed relative to those connections as they exist within the narrow gap between the IC package 1 and the circuit board 2, as shown in FIG. 2. In defining the practical implementation of such visual examination capability, the criterion was established that the field of view should encompass the conductor pins arranged in a zone of 5 mm along each side of the IC package 1.

Figure 4:
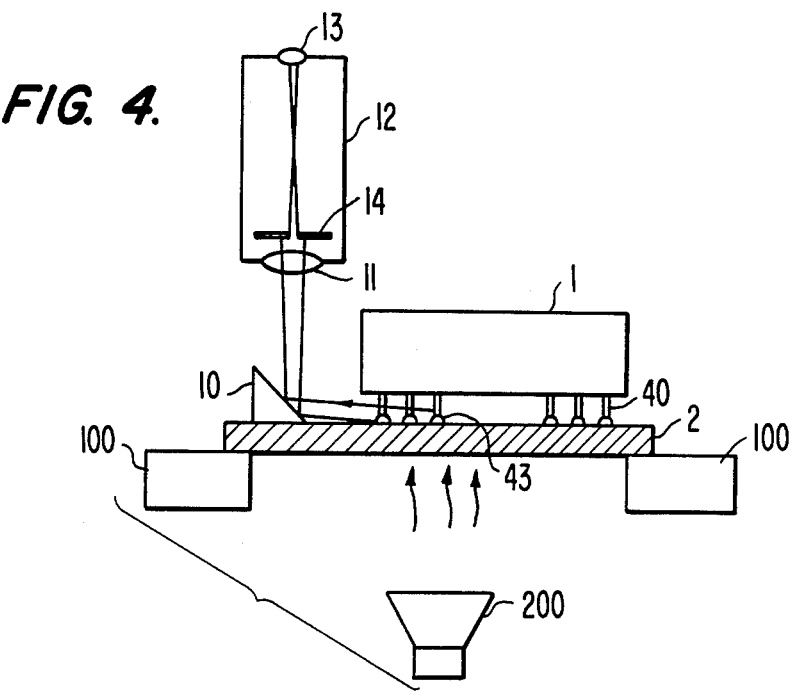
FIG. 4 is a schematic, elevational view of apparatus in accordance with the present invention, for facilitating an explanation of the method of the present invention.

FIG. 4 is a schematic, plan view of apparatus in accordance with the invention, useful for explaining the underlying principle of the method of operation for visual examination of the soldered connections between conductor pins and pads, in accordance with the present invention. In FIG. 4, a card comprising an IC package 1 and circuit board 2 is placed on a table 100. The bottom surface of the circuit board 2 is illuminated from beneath, through the opening in the table 100, by a flood of light provided by the light source 200. The light is transmitted through the circuit board 2 and is scattered in the gap between the IC package 1 and the circuit board 2, and then emitted from the edge of the gap, at the periphery of the IC package 1, as indicated by the arrows. The emitted light is deflected upwardly by a deflecting means 10, for example, a prism. The light deflected by the deflecting means 10 is collected and focused by a focusing means 11 to form an image of the solder joint 43, viewed through eyepiece 13 and an iris diaphragm 14 mounted within a lens barrel 12. IP 13, of course, provides for optically magnifying the image as well as focusing. In a practical device, the aperture diameter of the iris diaphragm 14 is selected to be approximately 2 mm, thereby to obtain a focusing depth of 5 mm, as is necessary for encompassing 5 in-line conductor pins within the field of view, for simultaneous observation.

The most successful results were achieved with the method of illumination illustrated in FIG. 4, as compared with alternative techniques employing direct illumination of the soldered connections by a flood of light or a scanning laser beam projected through the gap and thus parallel to the opposed, interior surfaces of the IC package 1 and the PCB 2. These alternate techniques present at least two significant disadvantages. The first is the strong halation which occurs at the unsoldered surface portions of the conductor pin 40, and which results in decreasing the visual contrast effect relating to the soldered portions. The second is the nonuniform intensity of illumination of the conductor pins which are spaced further from the light source, the decrease being greater than that determined by the reciprocal square of the distance from the light source, due to the occulation effect of the conductor pins nearer the edge of the gap relative to those positioned toward the interior. The illumination technique as illustrated in FIG. 4, in accordance with the method of the present invention, thus is preferable since it affords substantially uniform illumination of the soldered joints to be visually examined, by the scattered light within the gap.

Figure 5:
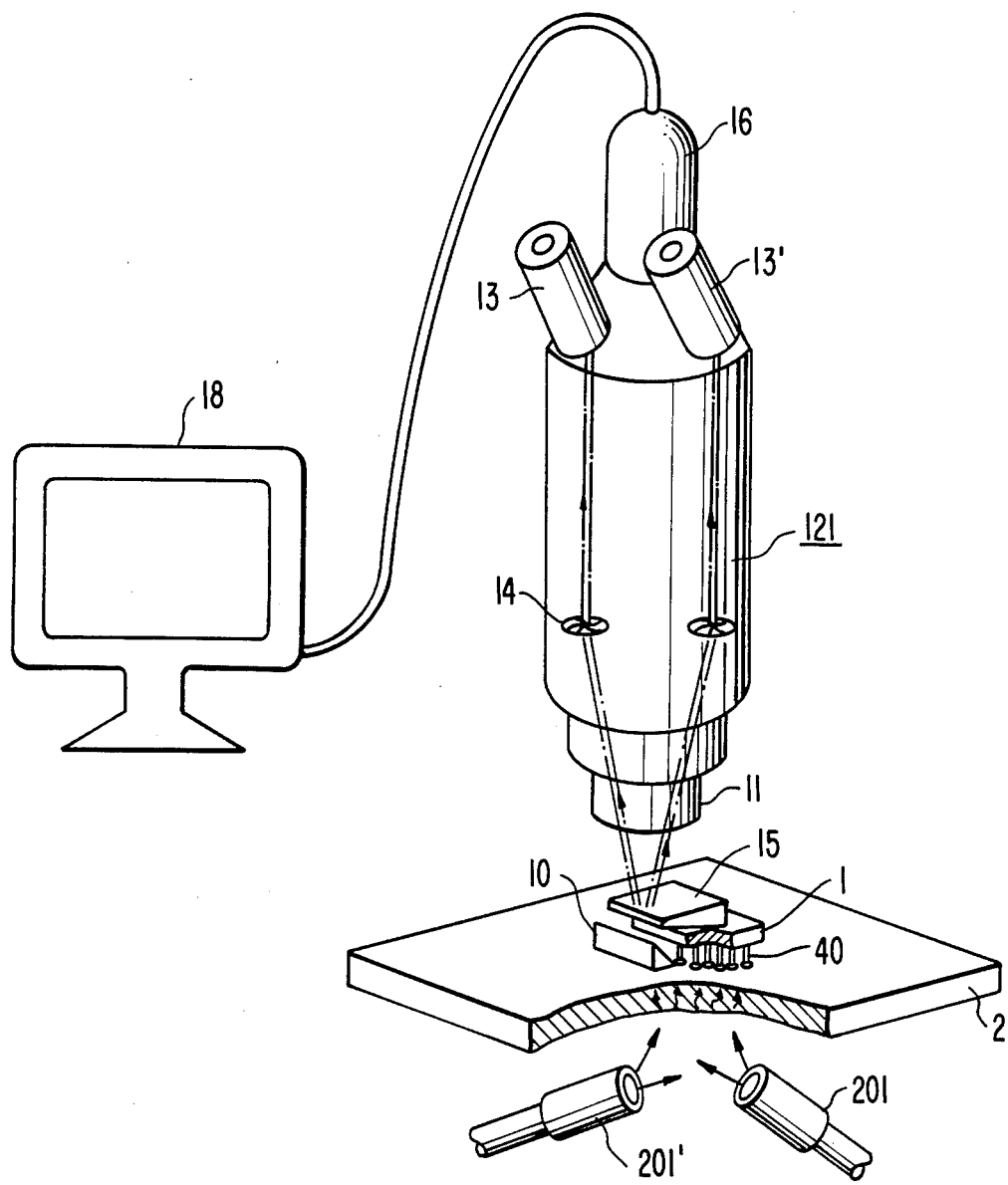
FIG. 5 is a perspective view, partially cut-away, of apparatus in accordance with the present invention.

FIG. 5 is a partially cutaway, perspective view of visual inspection apparatus according to the present invention. In FIG. 5, halogen lamps 201 and 201' correspond to the illuminating means 200 in FIG. 4, and are employed because their spectral distribution characteristics match the spectral transmission characteristics of the circuit board 2. The use of two halogen lamps 201 and 201', each of 100 watts, for example, produces a level of illumination of 400,000 lux on the back surface of the circuit board 2. A stereoscopic microscope 121 is used for the focusing means 11, affording a long focal length optical system which is capable of imaging five conductor pins of five corresponding rows (a range of 5 mm) simultaneously. As is well known, the stereoscopic microscope 121 affords not only focusing capability but also provides for optically magnifying the image, typically on the order of $\times 10$ to $\times 20$ relative to the image formed by the naked eye and $\times 4$ to $\times 8$ with respect to the video camera 16. In the practical observing apparatus, another prism 15, which provides a means for varying the viewing angle relative to the soldered joints, is positioned in the light path between the prism 10 and the stereoscopic microscope 121. (The details of the prisms 10 and 15 are described later.)

According to the apparatus as shown in FIG. 5, the images of the soldered joints in the gap beween the IC package 1 and circuit board 2 can be observed even when a number of other IC packages are mounted on the circuit board 2, provided there is sufficient space for accommodating the prism 10 between adjacent IC packages. The image of the soldered joints is observed through the eyepieces 13 and 13'. The image also can be projected on the photoelectric transducer of a video camera 16, whereby it can be displayed on a video terminal 18, if desired.

Figure 6A:
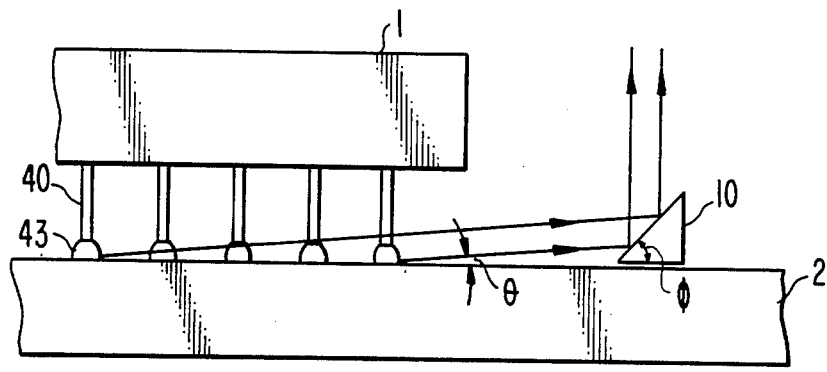
FIG. 6A is an enlarged, elevational view, partially cut-away, of a portion of the apparatus of FIG. 5, illustrating a method for determining certain light transmission angles of the light emitted from the gap, and the corresponding deflection angle required for subsequent focusing and imaging.

FIG. 6A is a simplified and schematic elevational view, in section, of the apparatus of FIG. 5, useful for explaining a suitable method for determining the appropriate angles of deflection of the light emitted from the gap. To observe the full profile of the soldered joint 43 of the fifth pin, spaced apart by about 6 mm from the edge of the 1.5 mm gap between the IC package 1 and circuit board 2, the light emitted from the pin must enter the reflecting surface of the prism 10 with an angle of elevation, $\theta$. The value of $\theta$ has been empirically determined to be 5°. To provide that the light is reflected upwardly in a direction substantially perpendicular to the surface of the circuit board 2, the reflecting surface of the prism 10 is selected to have an angle of inclination, φ=42.5°, with respect to the surface of the circuit board 2.

Figure 6B:
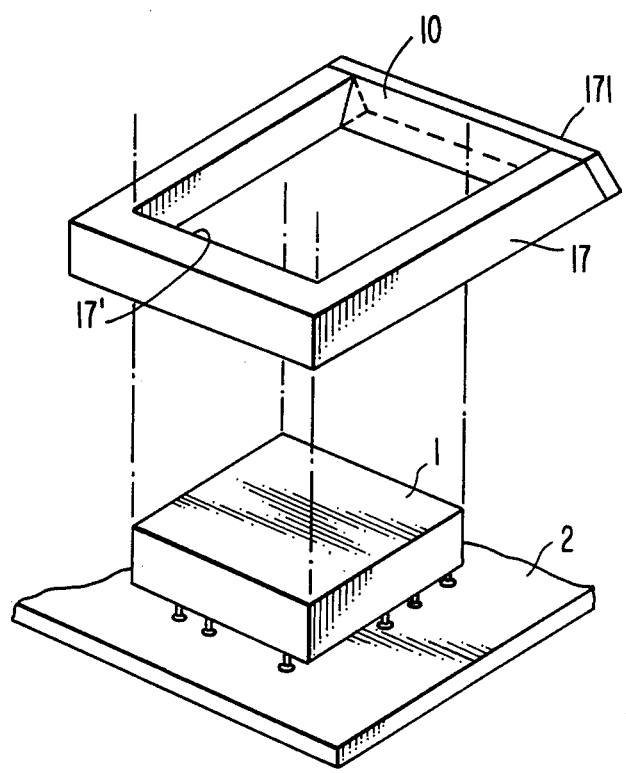
FIG. 6B is a simplified and partially broken away, perspective view of a jig and associated prism for facilitating the positioning of the prism in accordance with the requirements of the apparatus and the performance of the method of this invention.

FIG. 6B is a simplified, perspective view, partly in section, of a jig comprising a frame 17 and a supporting plate 171 backing up the prism 10, useful for conducting the visual examination described with reference to FIG. 6A. Particularly, the frame 17 in conjunction with the prism 10 defines a central, rectangular opening adapted to be received about the periphery of the IC package 1, such that the inner side surface 17' thereof opposite that of the prism 10 contacts the IC package 1 and thereby maintains a fixed relative position of the prism 10 with respect to the IC package 1.

Figure 7A:
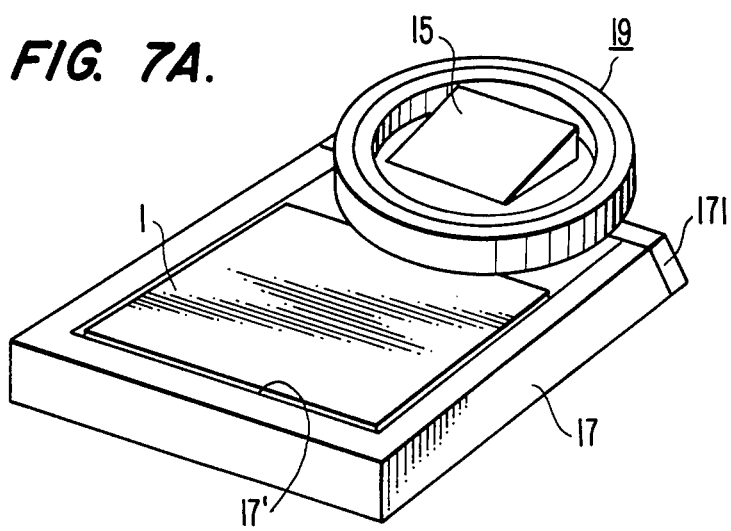
FIGS. 7A and 7B are perspective and elevational views, respectively, the latter in partial cross-section, of a jig and related prism and adjustment elements for varying the visual angle of examination relative to the objects to be examined in accordance with the method and the apparatus of the present invention.
Figure 7B:
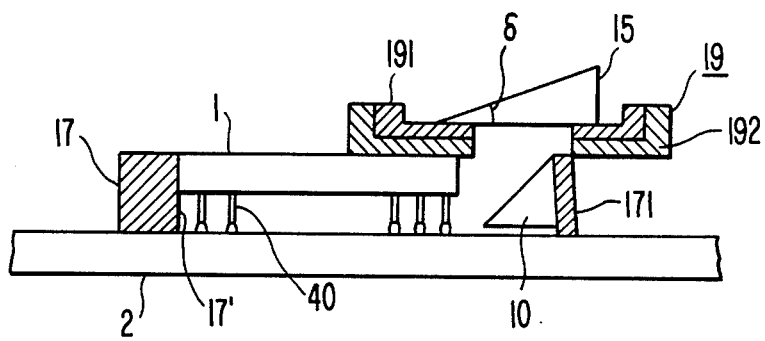

FIGS. 7A and 7B are perspective and elevational views, respectively, the latter in partial cross-section, of a means for varying the angle of observation, relative to the objects. There is a requirement to vary the visual angle of observation, because of instances wherein certain conductor pins are hidden behind other conductor pins and thus cannot be observed separately from the others. The visual angle of observation, relative to the aligned column (or row) of conductor pins 40, can be changed by moving the circuit board 2 with respect to the focusing means 11 by using the table 100 in FIG. 4. However, this requires a very precise control such that the necessary amount of displacement for the circuit board is achieved, and clearly decreases the speed of operation of the examination of successive IC packages. Thus, it is a considerable advantage to be able to vary the visual angle of observation relative to the conductor pins 40 without having to change the relative position of the IC package 1 and the circuit board 2 relative to the supporting table 100. For this purpose, a second deflecting means, for example a prism 15, is positioned between the prism 10 and the focusing means 121 (see FIG. 5). The prism 15 has a pair of planes displaced from each other by an angle δ=5° for example, and intersects the path of light reflected by the prism 10. A prism holder 19 comprises an inner ring 191 on which the prism 15 is mounted. The inner ring 191 is mounted within the outer shell 192 for selective, relative rotation. Therefore, when the inner ring 191 is rotated together with the prism 15, the outgoing direction of the light from the prism 15 varies. In other words, the source of the incoming light to the focusing means changes with the rotation of the prism 15, thus permitting visual examination of those soldered joints which previously were impeded or hindered.

Figure 8A:
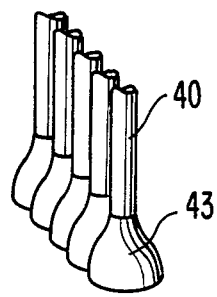
FIGS. 8A and 8B are illustrations of images of the objects as formed for visual inspection in accordance with different visual angles, as afforded by the structure illustrated in FIGS. 7A and 7B.
Figure 8B:
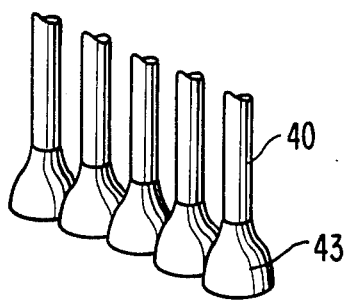

The effect of the deflecting means 15 is illustrated in FIGS. 8A and 8B. Each of FIGS. 8A and 8B shows the soldered joints 43 of the aligned conductor pins 40, corresponding to a selected column of five pins, one from each of five rows of conductor pins as arranged along the edge of an IC package. In FIG. 8A, which illustrates the image produced without use of the prism 15, the profile of each of the soldered joints 43 cannot be observed separately. However, in FIG. 8B, which illustrates the image produced by selective rotation of the prism 15, there results sufficient separation of the profiles of the solder joints 43 to permit adequate visual examination.

Although the invention has been described with a certain degree of particularity in the foregoing in relation to a specific preferred embodiment of the invention, numerous modifications and adapations thereof will be apparent to those of skill in the art and thus it is intended by the appended claims to encompass all such modifications and adaptations which fall within the true spirit and scope of the invention.

I claim:

1. A method for visually examining a plurality of objects disposed to extend transversely of a gap approximately 1.5 mm defined between first and second generally parallel, spaced plates having respective, substantially flat inner surfaces facing the gap, the first plate being light transmissible and having an outer surface generally parallel to the inner surface thereof, comprising the steps of:
    illuminating the outer surface of the first plate to produce diffused light within the gap which illuminates the objects and is emitted from an edge of the gap,
    deflecting the light emitted from the edge of the gap in a direction substantially perpendicular to the inner surface of the first plate; and
    focusing the emitted light to form an image of a selected number of the objects.

2. A method as recited in claim 1 wherein said focusing step further comprises optically magnifying the image.

3. The method as recited in claim 1 wherein the focusing step further comprises:
    focusing the emitted light to form the image on a photosensitive surface of a photoelectric transducer for providing electrical signals corresponding to the image; and
    producing a visual display of the images from the electrical signal.

4. A method as recited in claim 1, further comprising:
    further deflecting the light through a selected angle of rotation about an axis defined by the said substantially perpendicular direction to adjust the relative displacement of adjacent objects in the image.

5. An apparatus for visually examining a plurality of objects disposed to extend transversely of a gap approximately 1.5 mm defined between first and second, generally parallel, spaced plates having respective, substantially flat inner surfaces facing the gap, the first plate being light transmissible and having an outer surface generally parallel to the inner surface thereof, comprising:
    means for illuminating the outer surface of the first plate to produce diffused light within the gap which illuminates the objects and is emitted from an edge of the gap;
    means for deflecting the light emitted from the edge of the gap in a direction substantially perpendicular to the inner surface of the first plate; and
    means for focusing the emitted light to form an image of a selected number of the objects.

6. An apparatus as recited in claim 5 wherein said deflecting means comprises a prism having an angled reflecting plane disposed to intercept the light emitted from the gap, for deflecting the light emitted from the gap and transmitting same in the aforesaid substantially perpendicular direction.

7. An apparatus as recited in claim 5 wherein said focusing means comprises an optical microscope.

8. An apparatus as recited in claim 5, further comprising:
    selctively rotatable light deflecting means disposed between said light deflecting means and said focusing means and being selectively rotatable about an axis defined by said substantially perpendicular direction for deflecting light transmitted in said substantially perpendicular direction through a selected angle of deflection thereby to change the relative displacement of adjacent objects in the image.

9. An apparatus as recited in claim 8 wherein said selectively rotatable deflection means comprises:
 a prism having a pair of surfaces defining a predetermined acute angle therebetween, a first of said surfaces being disposed parallel to the inner surface of the first plate, and disposed to intercept the light transmitted in said substantially perpendicular direction from said light deflecting means; and
 means for selectively rotating said prism about said axis.

10. An apparatus as recited in claim 5 further comprising:
 transducer means for responding to the images produced by said focusing means and producing corresponding electrical signals representative of the image; and
 display means responsive to said electrical signals of said transducing means for producing a visual display of the image.

11. An apparatus as recited in claim 10, wherein:
 said transducing means comprises a video camera; and
 said display means comprises a video display screen.

12. Apparatus as recited in claim 7 wherein said illuminating means comprises a halogen lamp.

13. Apparatus for visually examining soldered connections formed between conductor leads of an integrated circuit package and corresponding connector pads of a printed circuit board, wherein the respective, opposing surfaces of the integrated circuit package and the printed circuit board are substantially flat and spaced apart to define a gap therebetween, the printed circuit board is light transmissible and has an outer surface generally parallel to the inner surface thereof, the conductor leads extend transversely across the gap from the inner surface of the integrated circuit package, and the connector pads are formed on the inner surface of the printed circuit board in positions corresponding to the conductor leads, comprising:
 means for supporting a printed circuit board having an integrated circuit package mounted thereon, with the inner surfaces of the package and the printed circuit board parallel to a first plane;
 means for illuminating the outer surface of the printed circuit board to produce diffused light within the gap, which illuminates the soldered connections and is emitted from an edge of the gap;
 first deflecting means selectively positionable in a plane parallel to said first plane and adjacent the inner surface of a printed circuit board, so as to receive light emitted from the gap and to deflect same in a direction substantially perpendicular to said first plane; and
 means for receiving and focusing said light transmitted in said substantially perpendicular direction, for forming an image of the soldered connections between the corresponding conductor leads and pads.

14. An apparatus as recited in claim 13, wherein said first light deflection means comprises a prism.

15. An apparatus as recited in claim 14, wherein:
 said light emitted from the gap relative to a soldered connection to be examined is at an angle of elevation of approximately 5° relative to the inner surface of a printed circuit board, and wherein:
 said prism is a right angle prism in cross-section, the right-angled surfaces thereof respectively being parallel and perpendicular to said first plane and the angled reflecting surface thereof being disposed to receive the light emitted from the gap, the angled reflecting surface having an angle of inclination of approximately 42.5° relative to said first plane.

16. An apparatus as recited in claim 14 wherein said first deflecting means comprises a jig supporting said prism as one edge thereof and defining an inner opening of a configuration corresponding to that of an integrated circuit package having soldered connections to be examined, and of dimensions to be received over and positioned about the integrated circuit package and onto the surface of the printed circuit board, for positioning the prism a predetermined distance from and parallel to the integrated circuit package edge from which light is emitted relating to the images to be examined.

17. An apparatus as recited in claim 13, further comprising:
 second light deflecting means positioned intermediate said first light deflecting means and said focusing means for intercepting the light transmitted by said first deflecting means in said substantially perpendicular direction and deflecting same through an angle of rotation about an axis defined by said perpendicular direction.

18. An apparatus as recited in claim 13, wherein:
 said first deflecting means comprises a first prism disposed parallel to an edge of the integrated circuit package having soldered connections which are to be examined, for deflecting light emitted from the edge of the gap and intercepted thereby in a direction substantially perpendicular to the inner surface of the first plate; and there is further provided
 second light deflecting means comprising a second prism and means for mounting said second prism for selective rotation, relative to said first prism, about an axis defined by said substantially perpendicular direction of light transmission as established by said first prism.

19. An apparatus as recited in claim 13, wherein said illuminating means comprises at least one halogen lamp having spectral characteristics corresponding to the light transmission characteristics of the printed circuit board.

20. An apparatus as recited in claim 13 wherein said focusing means comprises an optical microscope.

21. An apparatus as recited in claim 13, further comprising:
 a video camera for receiving images formed by said focusing means and producing corresponding electrical signals; and
 a video display for producing a visual display of the images represented by the signals produced by said video camera.

* * * * *